US00PP35653P2

(12) United States Plant Patent
Moucheboeuf

(10) Patent No.: US PP35,653 P2
(45) Date of Patent: Feb. 13, 2024

(54) ***DIANTHUS* PLANT NAMED 'WP22 ELECDR'**

(50) Latin Name: *Dianthus allwoodii hort.*
Varietal Denomination: WP22 ELECDR

(71) Applicant: Plant Genetics International, Ltd., Exeter (GB)

(72) Inventor: Laetitia Moucheboeuf, Devon (GB)

(73) Assignee: PLANT GENETICS INTERNATIONAL LIMITED, Exeter (GB)

( * ) Notice: Subject to any disclaimer, the term of this patent is extended or adjusted under 35 U.S.C. 154(b) by 0 days.

(21) Appl. No.: 18/184,661

(22) Filed: Mar. 16, 2023

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./273
See application file for complete search history.

(56) References Cited

PUBLICATIONS

CPVO Register—CPVO Application Consultation; Citation for 'WP22 ELECDR'; version 4.9.16 (Retrieved from the Internet on Jul. 10, 2023) (3 pages total).*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new cultivar of *Dianthus* plant named 'WP22 ELECDR' that is characterized by a compact mounding habit, single pink flowers, tri-band like pattern, blooming from May through October, with a light fragrance, glaucous blue green foliage, suitable for use as a flowering plant in pots and containers, is disclosed.

2 Drawing Sheets

Genus and species: *Dianthus allwoodii hort.*
Variety denomination: 'WP22 ELECDR'.

BACKGROUND OF THE NEW PLANT

The present invention relates to a new and distinct cultivar of hardy *Dianthus*, commonly known as Alpine Pink, which is grown for use as a flowering plant for pots and containers and for planting in the garden and landscape. The new cultivar is known botanically as *Dianthus allwoodii hort* and will be referred to hereinafter by the cultivar name 'WP22 ELECDR'.

'WP22 ELECDR' is a complex hybrid plant that is the product of a long-term breeding program conducted in a cultivated area of Ashcombe Road, Dawlish, Devon, United Kingdom. 'WP22 ELECDR' was selected in 2017 for its very compact form covered with a huge amount of single tri-band pink tones colored flowers, light clove like fragrance and glaucous grey-green foliage.

'WP22 ELECDR' arose and was selected as a seedling which resulted from the cross pollination of two breeder stock *Dianthus*, grown within the inventor's stock of breeding lines. The female parent is *Dianthus* code name 'WAD12248' (unpatented and unreleased). The male parent is *Dianthus* code name 'DEV10160' (unpatented and unreleased).

Asexual reproduction of 'WP22 ELECDR' was first accomplished in 2017 in a cultivated area of Ashcombe, United Kingdom using the propagation method of shoot cuttings. 'WP22 ELECDR' has been determined to be stable and reproduces true to type in successive generations of asexual propagation.

SUMMARY

The following traits have been repeatedly observed and represent the characteristics of the new *Dianthus* cultivar 'WP22 ELECDR'. 'WP22 ELECDR' has not been tested under all possible conditions and phenotypic differences may be observed with variations in environmental, climatic and cultural conditions, however, without any variance in genotype.

1. 'WP22 ELECDR' exhibits a compact mounding habit.
2. 'WP22 ELECDR' bears small single flowers with a tri-colored band.
3. The petals of 'WP22 ELECDR' are flat.
4. 'WP22 ELECDR' blooms from May through October.
5. The flowers of 'WP22 ELECDR' exhibit a light, clove like fragrance.
6. 'WP22 ELECDR' exhibits glaucous grey green foliage.
7. At maturity, the height of the foliage mound of 'WP22 ELECDR' is 13 cm to 15 cm, and the width is 16 cm to 20 cm.
8. 'WP22 ELECDR' is perennial and is hardy at least to minus 15° Centigrade.
9. 'WP22 ELECDR' is suitable for use as a flowering plant in pots, containers and borders.

BRIEF DESCRIPTION OF THE PHOTOGRAPHS

The accompanying color photographs illustrate the overall appearance of the new *Dianthus* variety 'WP22 ELECDR' showing colors as true as it is reasonably possible to obtain in colored reproductions of this type. Colors in the photographs may differ from the color values cited in the detailed botanical description, which accurately describe the actual colors of the new variety 'WP22 ELECDR'.

Figure 1:
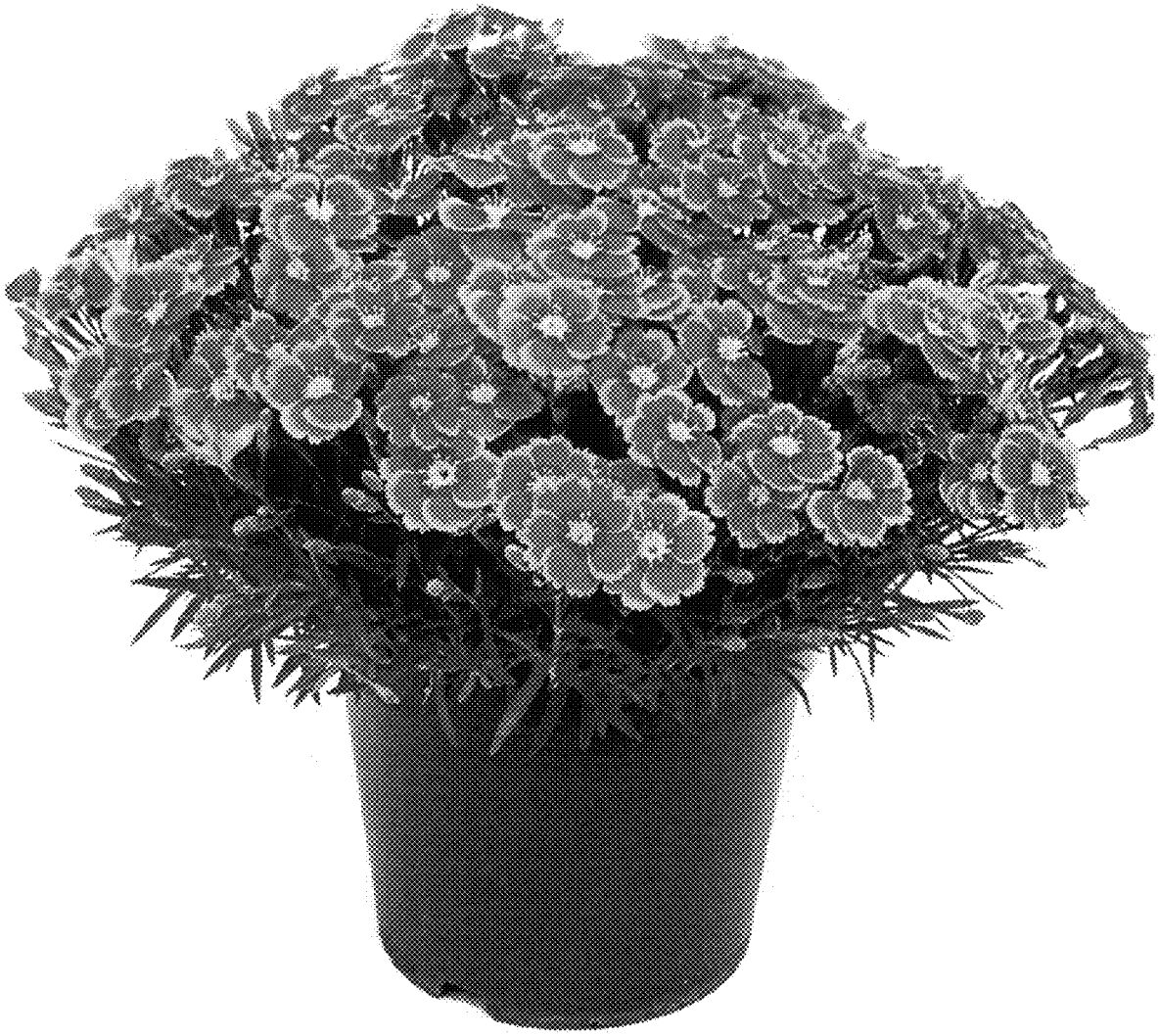
FIG. 1 depicts an entire flowering plant of 'WP22 ELECDR'.
Figure 2:
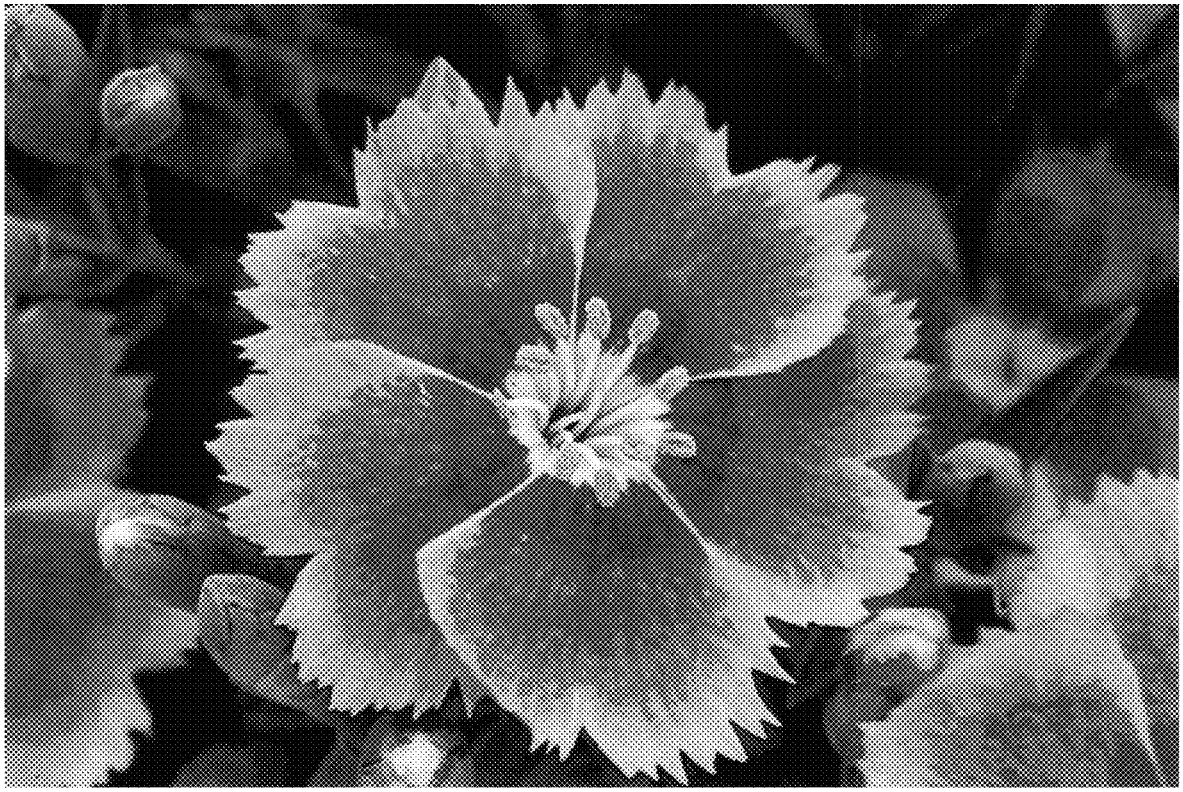
FIG. 2 depicts a close-up view of the flower of 'WP22 ELECDR'.

Photographs were taken in June 2020 in Dawlish, Devon, UK of a nine-month old plant grown indoors in 3-liter container. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP22 ELECDR'. Data was collected from plants grown in 3-liter containers under an unheated glasshouse in Ashcombe, Dawlish, United Kingdom. The color determinations are in accordance with the sixth edition (2015) of The Royal Horticultural Society Color Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

- *Variety*.—'WP22 ELECDR'.
- *Species*.—x *allwoodii*.
- *Common names*.—Hybrid *Dianthus*, Alpine Pink.
- *Commercial classification*.—Hardy perennial.
- *Use*.—Ornamental plant for pots and containers.

Parentage: 'WP22 ELECDR' is a hybrid plant that resulted from the cross-pollination of two *Dianthus* x *allwoodii* plants.

- *Female parent plant*.—'WAD12248' experimental *Dianthus* plant (unpatented).
- *Male parent plant*.—'DEV10160' experimental *Dianthus* plant (unpatented).

Plant description:

- *Bloom period*.—May to October.
- *Plant habit*.—Compact mounding habit.
- *Plant height*.—13 cm. to 15 cm. in overall height, including flower canopy.
- *Plant width*.—16 cm. to 20 cm. in width.
- *Plant hardiness*.—Hardy to minus 15° Centigrade.
- *Type*.—Perennial.
- *Root system*.—Fibrous.
- *Propagation*.—Propagation is accomplished using shoot cuttings.
- *Cultural requirements*.—Plant in full sun, well-drained and moderately fertile soil and keep well fertilized and watered.
- *Time required to produce a rooted cutting*.—5 weeks are needed to produce a rooted cutting.
- *Temperature recommended for cuttings to produce roots*.—The air temperature needed is a minimum of 15° Centigrade air temperature and base heat of 21° Centigrade.
- *Crop time*.—6 to 9 months is needed to produce a finished 3-litre container size from a well-rooted cutting.

Stem:

- *Shape*.—Cylindrical, solid.
- *Dimensions*.—3.5 cm. to 4 cm. in length, 4 mm. diameter.
- *Surface*.—Glabrous and glaucous.
- *Color*.—138C and 138D (in the sheathing zone).
- *Branching*.—Numerous shoots from the axils of the lower leaves.
- *Internode length*.—About 1 mm. between nodes (before extension of peduncle).
- *Node dimensions*.—3 mm. in diameter and 1 mm. in length.

Leaf:

- *Type*.—Evergreen.
- *Dimensions*.—3.5 cm. in length, 4 mm. in width.
- *Color adaxial surface*.—189A and N138A.
- *Color abaxial surface*.—N138A.
- *Shape*.—Linear to sword-shaped.
- *Division*.—Simple.
- *Apex*.—Acute.
- *Base*.—Decurrent.
- *Venation*.—Absent on the adaxial surface and only one central vein visible on the abaxial surface.
- *Margins*.—Entire.
- *Attachment*.—Sheathing.
- *Arrangement*.—Opposite and spiraling up stem.
- *Surfaces* (*adaxial and abaxial*).—Glaucous.
- *Fragrance*.—Absent.

Flowers:

- *Inflorescence*.—Simple cyme.
- *Type*.—Single, polypetalous.
- *Number*.—2 to 5 per stem.
- *Dimensions* (*including calyx*).—22 mm. in length and 31 mm.-33 mm. in diameter.
- *Shape*.—Circular.
- *Lastingness*.—10 days at 20° Celsius on the plant; 8 to 10 days off the plant.
- *Fragrance*.—Light, clove like.
- *Flowering period*.—May to October.

Peduncle:

- *Shape*.—Cylindrical, solid.
- *Dimensions*.—About 10 cm. in length, 1 mm. in diameter.
- *Surface*.—Glabrous, waxy.
- *Strength*.—Strong, rigid.
- *Color*.—N138C.

Bud:

- *Shape*.—Ovate.
- *Color*.—N138B to N138C on apical half and 144B to 144C on basal half (below the bracts).
- *Anthocyanin*.—Present, as a hue.
- *Dimensions*.—16 mm. in length and 4 mm. in width (at breaking color point).

Petals:

- *Corolla*.—Upper and lower part of corolla is flat.
- *Petal arrangement*.—Persistent, apopetalous and overlapping.
- *Margin*.—Crenate-dentate.
- *Indentations*.—Up to 1 mm. deep along the margin with a deeper indentation up to 3 mm. deep in the middle of the petal, making the petal into a kind of heart shape.
- *Texture*.—Soft.
- *Type*.—Single.
- *Number of petals*.—5.
- *Dimensions*.—About 32 mm. in length, 19 mm. in width.
- *Petal shape*.—Fan shape.
- *Petal surface*.—Glabrous.

*Petal apex.*—Fan shaped, crenate-dentate.
*Petal base.*—Strap shaped, tapering towards base.
*Color pattern.*—Blade has 3 colors organized like a tri-band, pink tones.
*Petal color* (*adaxial surface*).—Ground color of blade: NN66A with the outer edge of the petal being 73A, distributed on the margin. Color of band: 71A, slightly hairy. Color of middle of strap: 144D. Color of base of strap: 149D.
*Petal color* (*abaxial surface*).—Ground color of blade: Closest 75B. Color of middle of strap: 144D. Color of base of strap: 149D.

Calyx:
*Dimensions.*—15 mm. in length and 4 mm. in width.
*Shape.*—Cylindrical and straight.
*Sepals.*—5, fused up to 3 mm. below the apex.
*Sepal dimensions.*—5 mm. in length and 3 mm. in width.
*Apex.*—Acute.
*Base.*—Truncate.
*Color of sepals, outer surface.*—138B to 138C on apical half and 138C, 144C, 144D on basal half (below the bracts).
*Color of sepals, inner surface.*—139D.
*Anthocyanin.*—Present, as a hue.
*Splitting.*—Not observed.

Epicalyx:
*Number of bracts.*—1 pair of 2.
*Bracts shape.*—Acute.
*Bracts dimensions.*—5 mm. in length and 5 mm. in width.
*Bracts color.*—N138B, N138C and 144B, 144C are all present.
*Anthocyanin.*—Absent.
*Number of bracteoles.*—1 pair of 2.
*Bracteoles shape.*—Medium acuminate.
*Bracteoles dimensions.*—5 mm. in length and 7 mm. in width.
*Bracteoles color.*—N138B, N138C and 144B, 144C are all present.
*Bracteoles anthocyanin.*—Absent.

Reproductive organs:
*Stamen number.*—10.
*Stamen dimensions.*—20 mm. length and 0.5 mm. diameter.
*Color of filaments.*—Whiter than NN155D.
*Anther number.*—10.
*Anther dimensions.*—2 mm. length and 0.5 mm. in diameter.
*Color of anthers.*—Closest 76B (when fresh anthers).
*Anther attachment.*—Dorsifixed.
*Pollen.*—Present, closest 92D and 202D.
*Style number.*—2.
*Style shoulder.*—Absent.
*Color of style.*—Whiter than NN155D.
*Style and Stigma dimensions.*—15 mm. to 20 mm. in length and 0.5 mm. in width.
*Stigma number.*—One on each style.
*Stigma color.*—75A and 75B.
*Stigma dimensions.*—About 5 mm. long along the top of the style, fimbriated zone, few mm above petals at maturity, terminating with slight bifid protuberance.
*Ovary position.*—Superior.
*Ovary dimensions.*—5 mm. in length and 2 mm. in diameter.
*Ovary shape.*—Oblong.
*Ovary surface and texture.*—Smooth and slightly ribbed.
*Ovary color.*—144D at the uppermost surface, becoming paler into 145D at the lowest surface.

Seed:
*Color.*—202A.
*Length.*—4 mm.
*Diameter.*—3 mm.
*Shape.*—Oval and flattened.
*Surface.*—Crinkled.
*Number.*—Varies, up to 15 per pod.

Diseases and pests: Susceptible to known *Dianthus* pests and disease but no other susceptibilities to pests or disease are known.

COMPARISON WITH PARENTAL LINE AND KNOWN VARIETY

'WP22 ELECDR' is distinguishable from the female parent as follows. The female parent 'WAD12248' bears bright pink flowers with a very small dark pink band. The petal edges are also bordered with a very light pink edge. The flower diameter of the female parent is also wider than 'WP22 ELECDR', as well as the female parent's overall plant size.

'WP22 ELECDR' is distinguishable from the male parent as follows. The male parent 'DEV10160' bears light pink flowers with a darker pink band, with a peak like in the middle of each petal. Also of similar height, the plant is smaller and less vigorous than 'WP22 ELECDR' and bears much less flowers.

The variety of *Dianthus* considered to resemble most closely 'WP22 ELECDR' is *Dianthus* Plant Named 'Noreen' (U.S. Plant patent application Ser. No. 20,369 P2). In comparison with 'Noreen', 'WP22 ELECDR' bears single tri-colored pink flowers and has a much more compact vegetative part. The foliage color of 'WP22 ELECDR' is also greener compared to 'Noreen', which is more grey-green.

I claim:

1. A new and distinct cultivar of *Dianthus* Plant Named 'WP22 ELECDR' as described and illustrated herein.

* * * * *